(12) United States Patent
Beselt et al.

(10) Patent No.: US 8,561,468 B2
(45) Date of Patent: Oct. 22, 2013

(54) SCANNER DIAGNOSTICS UTILIZING THREE AXIS ACCELEROMETERS

(75) Inventors: Ron Beselt, Burnaby (CA); Cris Andronic, Burnaby (CA)

(73) Assignee: Honeywell ASCa Inc., Mississauga (CA)

( * ) Notice: Subject to any disclaimer, the term of this patent is extended or adjusted under 35 U.S.C. 154(b) by 284 days.

(21) Appl. No.: 13/170,175

(22) Filed: Jun. 27, 2011

(65) Prior Publication Data

US 2012/0325002 A1 Dec. 27, 2012

(51) Int. Cl.
*G01H 17/00* (2006.01)
*G01D 11/00* (2006.01)
*G01F 1/56* (2006.01)

(52) U.S. Cl.
USPC ............... 73/570; 73/159; 73/866.5; 702/182

(58) Field of Classification Search
USPC ........ 73/570, 593, 159, 866.5, 600, 602, 659, 73/660; 702/57, 66, 182–185
See application file for complete search history.

(56) References Cited

U.S. PATENT DOCUMENTS

| | | | |
|---|---|---|---|
| 4,595,384 A | 6/1986 | Tertinek | |
| 4,891,611 A * | 1/1990 | Frerking | 331/158 |
| 4,980,844 A | 12/1990 | Demjanenko | |
| 5,166,748 A | 11/1992 | Dahlquist | |
| 5,195,046 A * | 3/1993 | Gerardi et al. | 702/35 |
| 5,602,757 A | 2/1997 | Haseley | |
| 5,654,799 A | 8/1997 | Chase | |
| 5,663,894 A * | 9/1997 | Seth et al. | 702/56 |
| 5,773,714 A | 6/1998 | Shead | |
| 5,793,486 A | 8/1998 | Gordon | |
| 5,995,910 A * | 11/1999 | Discenzo | 702/56 |
| 6,041,287 A * | 3/2000 | Dister et al. | 702/182 |
| 6,253,604 B1 * | 7/2001 | Henry et al. | 73/159 |
| 6,289,735 B1 | 9/2001 | Dister | |
| 6,517,439 B1 | 2/2003 | Sears | |
| 6,536,270 B1 * | 3/2003 | Henry et al. | 73/159 |
| 6,636,817 B2 * | 10/2003 | Fioravanti | 702/75 |
| 7,394,385 B2 | 7/2008 | Franco, Jr. | |
| 7,487,401 B2 | 2/2009 | Urmanov | |
| 7,494,567 B2 | 2/2009 | Haran | |
| 7,599,427 B2 | 10/2009 | Bik | |
| 7,789,348 B2 | 9/2010 | Ruggiero | |
| 7,819,009 B2 | 10/2010 | Borah | |
| 7,819,034 B2 * | 10/2010 | Jasinski | 73/866.5 |
| 7,944,582 B2 | 5/2011 | Kato | |

* cited by examiner

*Primary Examiner* — J M Saint Surin
(74) *Attorney, Agent, or Firm* — Cascio Schmoyer & Zervas

(57) ABSTRACT

Numerous failure modes, causes, and adverse operating conditions on scanner systems exhibit mechanical signatures that are detected by three-axis accelerometers located in the upper and lower sensor heads. A diagnostic system for monitoring the scanning system that detects characteristics of sheet materials during linear translation along a translation axis of a bi-directionally driven mobile detector device includes a vibration sensor configured to measure vibrations generated by various components of the scanning system and to generate vibration signals indicative of operation conditions of the components. Correlating the vibration signals to modes of operations of the components identifies the source, location and severity of potential problems in the scanner. In dual scanning systems, the accelerometer in the upper scanner head monitors activities associated with movement of the upper carriage while the accelerometer in the lower scanner head monitors activities associated with movement of the lower carriage.

22 Claims, 4 Drawing Sheets

SCANNER DIAGNOSTICS UTILIZING THREE AXIS ACCELEROMETERS

FIELD OF THE INVENTION

The present invention generally relates to scanner measurement systems for determining parameters of continuous sheet materials during production and, more particularly, to techniques for analyzing mechanical signatures in diagnosing the scanner's operation condition.

BACKGROUND OF THE INVENTION

Various sensor systems have been developed for detecting sheet properties "on-line," i.e., on a sheet-making machine while it is operating. Sensors for continuous flat sheet production processes typically employ single or dual-sided packages with on-line sensors that traverse or scan traveling webs of sheet material during manufacture. With dual scanners, the heads or assemblies are fixed to beams of a scanner frame system that span both sides of the sheet with linear guidance tracks to allow the sensors to move in unison in the cross direction, i.e., in the direction perpendicular to the direction of sheet travel. Depending upon the sheet-making operation, cross-directional distances can range up to about twelve meters or more. In the paper making art, for instance, the on-line sensors detect variables such as basis weight, moisture content, and caliper of sheets during manufacture. There is a desire to provide a method of monitoring the operating condition of the scanner frame system in order to provide early warning of component failure, contaminant buildup, or other detrimental operation conditions. Scanner heads are equipped with alignment or head displacement sensors that provide differential head displacement readings. However, such readings do not disclose the source of the misalignment. The main obstacle is that the potential failure modes are numerous with even more causes to those failure modes and therefore instrumenting a scanning frame for each individual cause is resource prohibitive.

SUMMARY OF THE INVENTION

The present invention is based in part on the demonstration that numerous failure modes, causes, and adverse operating conditions on scanner systems have a mechanical signature that can be detected through the use of accelerometers that can be located remotely from the machine components being monitored. In particular, the addition of a three-axis accelerometer in each of the upper and lower sensor heads aids in the diagnostics of the scanner's operation conditions. Sources of adverse operating conditions and associated mechanical vibrations include, for example, the accumulation of debris and/or the presence of foreign objects in the scanner system. Contaminant buildup on the tracks on which the carriage travels interferes with the movement of the carriage rollers. The presence of foreign objects disrupts the directional movement of the scanner head and other parts of the scanner system. With the present invention, impact of a sensor head with a foreign body can be detected and acted upon as an abnormal situations requiring immediate drive system shutdown. Similarly, motor malfunctions that cause sudden acceleration, for instance, can be monitored and appropriate motor drive tuning can be implemented.

Resonant vibrations in the beam structures of the scanner system can be monitored. Resonance can be located in the upper or lower beam and other structures of the scanner system and once the onset of resonant vibration is detected and the resonant frequencies determined, appropriate de-tuning actions can be taken. In a similar vein, the components of the drive mechanism can be monitored. For instance, problems associated with drive pulley eccentricity and with drive bearing and belts generate mechanical signatures that can be detected.

The present invention can also be used during manufacture to confirm that the scanner system has been properly assembled. For example, the motor and encoder wiring and systems parameters must be correctly configured to produce the correct motion by the host control computer. Thus, as part of the directional setup process, the scanner motion direction can be independently observed by the accelerometer readings.

In one aspect, the present invention is directed to a diagnostic system for monitoring a scanning system that detects characteristics of a sheet of material during linear translation along a translation axis of a bi-directionally driven mobile detector device, said diagnostic system including:

(a) the scanning system being monitored which includes:
 (i) a first elongated member that extends along a first direction wherein the first elongated member supports the first carriage that is mounted thereon; and
 (ii) means for driving the first mounted carriage, that supports a first sensor head, along a main scanning direction;

(b) a vibration sensor configured to measure vibrations generated by one or more components of the scanning system and generate vibration signals indicative of operation conditions of the one or more components; and (c) means for correlating the vibration signals to modes of operations of the one or more components of the scanning system.

In another aspect, the invention is directed to a method of diagnosing a mechanical condition of a scanning system that detects characteristics of a sheet of material during linear translation along a translation axis of a bi-directionally driven mobile detector device, wherein the scanning system being monitored includes (i) a first elongated member that extends along a first direction wherein the first elongated member supports a first carriage that is mounted thereon; and (ii) means for driving the first mounted carriage, that supports a first sensor head, along a main scanning direction, said method including the steps of:

(a) obtaining vibration signatures with a vibration sensor that are characteristic of one or more components of the scanning system; and (b) correlating the vibration signatures to modes of operations of the one or more components of the scanning system.

Preferred vibration sensors are three axis accelerometers that are positioned in the scanner heads that convert mechanical vibrations into acceleration readings.

DESCRIPTION OF PREFERRED EMBODIMENTS

Figure 1:
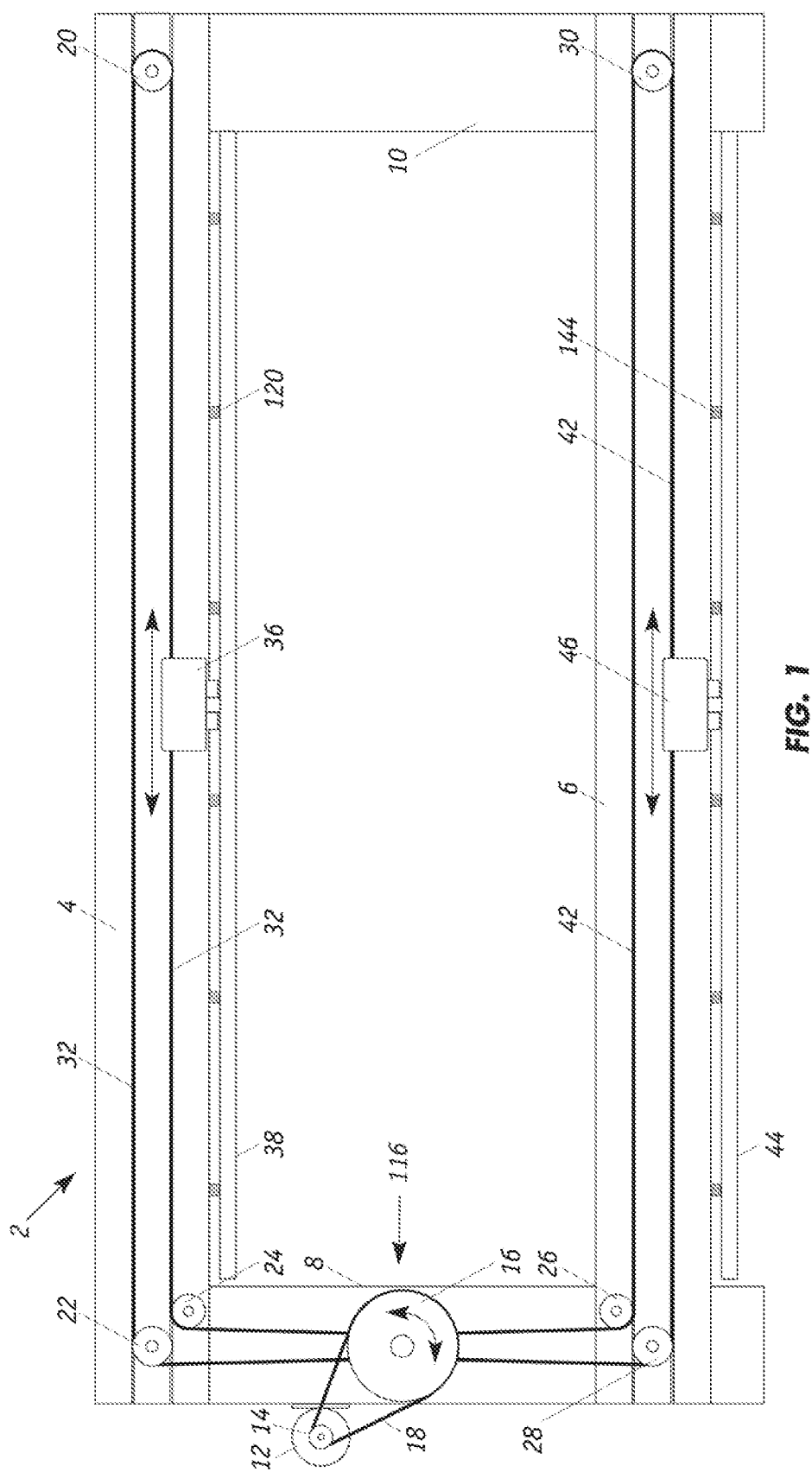
FIG. 1 illustrates a scanner system with parallel upper and lower support beams and drive mechanism.
Figure 2:
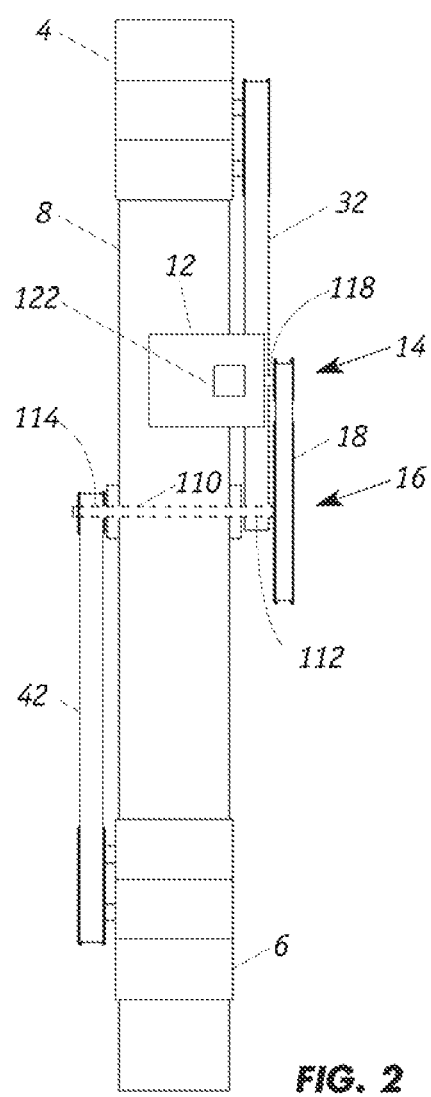
FIG. 2 is a side view of the scanner system depicting the motor of the drive mechanism.

FIGS. 1 and 2 show a scanner frame system 2 that has upper and lower support beams 4, 6 that are mounted onto a pair of upright end members 8, 10. Associated upper and lower suspended tracks 38 and 44 are secured to the lower surfaces of upper and lower support beams 4 and 6, respectively. In particular, a series of upper individual vertical support structures 120 support upper track 38 and a series of lower individual vertical support structures 144 support lower track 44. As described further herein, each track defines a path along which a sensor-mounted roller carriage travels. The tracks can sag along the intervals between the vertical support structures.

Upper support beam 4 is equipped with a plurality of upper fixed turning pulleys 20, 22 and 24 that are secured to the beam with pins. Each of the upper fixed turning pulleys preferably has a groove around its outer perimeter that is dimensioned to accommodate a flexible cable 32 which is round around the upper fixed turning pulleys and the proximal end 112 of drive shaft 110. Flexible cable 32 is connected to coupling device 36 that is attached an upper roller carriage (not shown.) Flexible cable 32 is secured with sufficient tension to avoid excessive slack and remains taut as it moves back and forth along the main scanning direction between end members 8, 10.

Similarly, lower support beam 6 is equipped with a plurality of lower fixed turning pulleys 26, 28 and 30 that are secured to the beam with pins. Each of the lower fixed turning pulleys has a groove around its outer perimeter that is dimensioned to accommodate a flexible cable 42 which is round around the lower fixed turning pulleys and the distal end 114 of drive shaft 110. Flexible cable 42 is connected to coupling device 46 that is attached a lower roller carriage (not shown.)

As further illustrated in FIGS. 1 and 2, common drive mechanism 116 for the roller carriages (not shown) includes a reversible electric motor 12 that is mounted on end member 8 and has a driven shaft 118 extending therefrom which rotates driven pulley 14. A gear belt 18 is looped over driven pulley 14 and drive or idler pulley 16; the center of idler pulley 16 is connected to drive shaft 110. Flexible cable 42 is looped over lower fixed turning pulley 28 and the distal end 114 of drive shaft 110 while flexible cable 32 is looped over upper fixed pulley 22 and the proximal end 112 of drive shaft 110. The diameters of the proximal and distal ends 112 and 114 of drive shaft 110 are the same so that the engagement of flexible cables 32, 42 to the ends 112, 114 enables motor 12 to generate the same amount of torque that is applied to each flexible cable. In this fashion, with the dual arrangement of the upper and lower fixed turning pulleys and their associated flexible cables, activation of motor 12 simultaneously engages both coupling devices 36 and 46. A rotary encoder 122 is mounted adjacent to motor 12 for motion feedback in tracking the position of motor shaft 118. In addition, the encoder is used to synchronize operations of the motor components. The configurations and dimensions for the upper and lower fixed turning pulleys are preferably the same so that coupling devices 36 and 46 move back and forth along parallel paths at the same speed and direction.

The constant and cyclic movement of the common drive mechanism can be readily monitored. For example, drive pulley eccentricity can cause periodic acceleration with the frequency being related to the pulley diameter and scanning speed. In addition, drive bearing or belt malfunctions generate high frequency vibrations that are transmitted via the drive belts to the scanner heads where they are detected by the accelerometers. The amplitude of the vibrations is typically too low for relative head displacement sensors to detect.

As part of the directional setup in the assembly process or during machine startup, the scanner motion direction can be independently observed by the acceleration readings to confirm that motor and encoder wiring and systems parameters are correctly configured to produce the correct motion by a host control computer.

Figure 3:
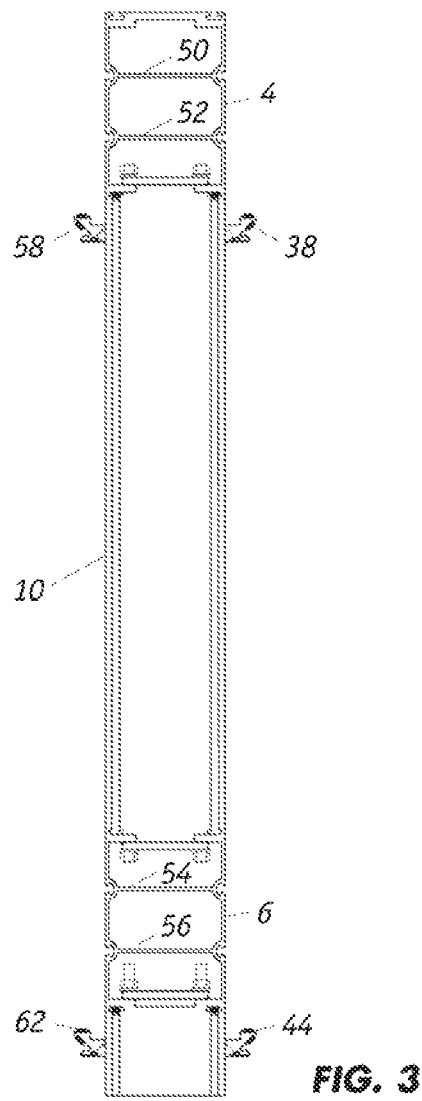
FIG. 3 is a cross sectional view of the upper and lower support beams.

As shown in FIG. 3, upper and lower structural support beams 4, 6 are mounted to a vertical end member 10 that is typically secured with bolts to a factory floor. Each single monolithic beam, with its hollow cross section, is preferably manufactured from extruded aluminum. In upper support beam 4, web members 50, 52 add structural integrity and provide lateral support during the extrusion manufacturing process by keeping the sides of the beam from deforming. Similarly, lower beam structure 6 includes interior web members 54, 56. The lengths of support beams 4, 6 typically range from 6 to 14 meters and more. Support beams 4, 6 are subject to fluctuations in environmental conditions with attendant temperature changes. The resulting thermal distortion of the beams, among other things, causes the radiation source and detector in dual scanner head systems, which are described further herein, to be misaligned. Resonance can occur in either upper or lower support beam. Vibration sensors can detect the onset of resonance and once the resonance frequencies are determined, appropriate de-tuning actions can be initiated.

Figure 4:
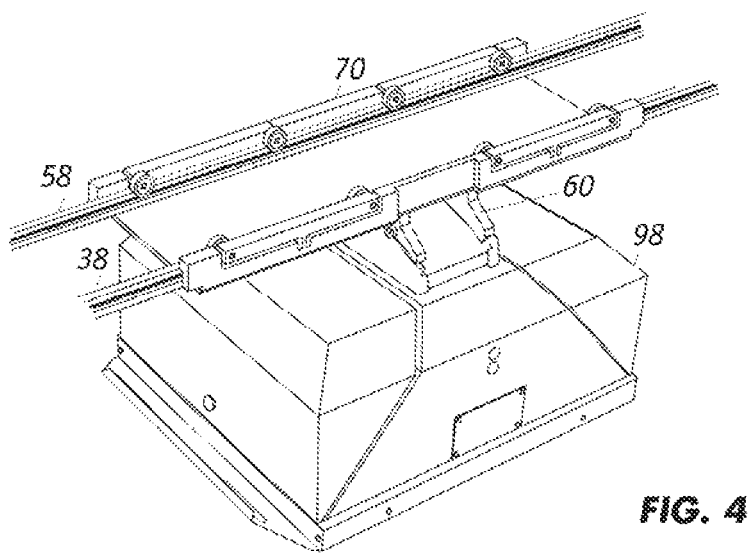
FIG. 4 shows a roller carriage positioned on a set of tracks and from which a sensor head is suspended.

The roller carriage used in the scanner system is particularly suited for transporting articles along a suspended track system, that is, one that is positioned above the ground. In this fashion, the roller carriage can transport a detection device traveling over a sheet or other material being monitored. As shown in FIG. 3, upper tracks 38, 58 and lower tracks 44, 62 define fixed paths for dual carriages (not shown). FIG. 4 depicts a set of suspended tracks 38, 58 dimensioned to accommodate the wheels of a roller carriage 70 that is transporting a sensor head 98 which is attached to the underside of the carriage via support assembly 60. Tracks 38, 58 define a fixed path in the main scanner direction through which carriage 70 transports the suspended sensor head 98. Movement of roller carriage 70 can be disrupted by discontinuities on the otherwise flat, low-friction track surfaces. In monitoring the condition of the tracks on which the carriage roller run, contaminant buildup will manifest as vibrational characteristics in the vertical axis acceleration. In a scanner system with dual scanner heads 98 and 102 as shown in FIG. 5, upper and lower tracks 38 and 44 are monitored by accelerometers 128 and 138, that are positioned in heads 98 and 102, respectively.

Figure 5:
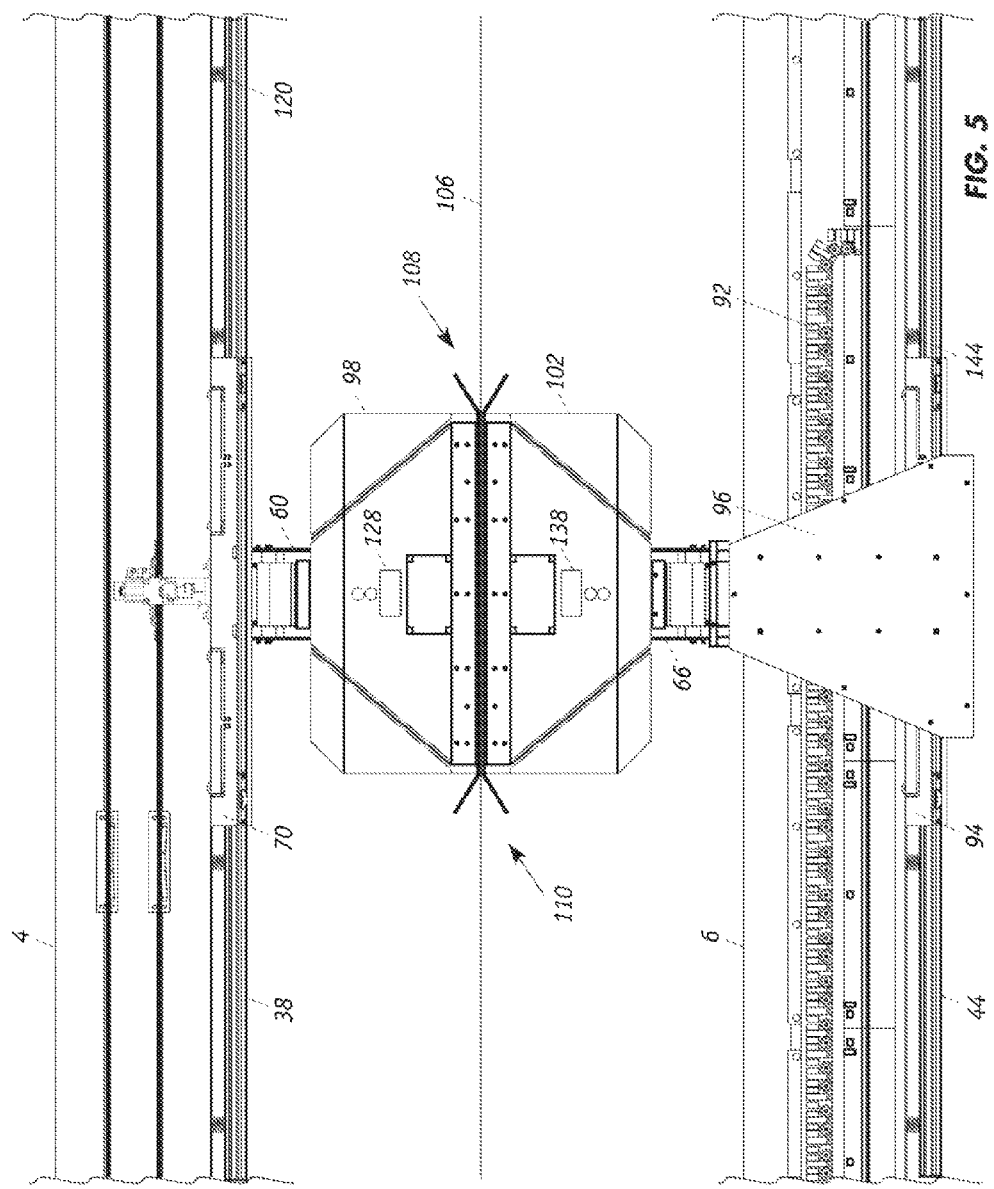
FIG. 5 is a side view of upper and lower structural beams of a scanning system with each beam supporting a roller carriage that supports one of the dual sensor heads.

FIG. 5 shows a scanning system with scanner sensor heads 98 and 102. This dual sensor configuration is typically employed when the sensor is operating in the transmissive mode. For example, upper sensor head 98 may house a source of infrared radiation while the lower sensor head 102 houses an infrared detector that measures the radiation that is transmitted through the material being monitored. The upper scanner head 98 is supported by an upper support beam 4, that has a lower surface to which a series of laterally spaced apart rigid support structures 120 is mounted. These vertical structures support track 38. The wheels of roller carriage 70 engage track 38 as the carriage advances along the cross direction to a moving sheet 106. Similarly, lower scanner head 102 is supported by a lower support beam 6, that has a lower surface on which a plurality of laterally spaced apart, rigid support structures 144 is mounted. These vertical structures support track 44 onto which the wheels of roller carriage 94 are engage. Movement of the roller carriage is facilitated by a drive mechanism similar to that of the upper scanner head. A power chain supplies 92 electricity and electrical signal to lower scanner head 102.

Lower sensor head 102 is secured to support assembly 66 which is mounted onto a member 96 that extends from roller carriage 94 so as to position lower sensor head 102 adjacent to upper scanner head 98. The operative faces of the lower and upper scanner heads 102, 98 define a gap with an entry 108 and exit 110 through which a web of material 106, that is moving in the machine direction, passes. The movements of the dual scanner heads 102, 98 are synchronized with respect to speed and direction so that they are aligned with each other. Scanning systems having sensor components on opposite sides of the sheet being analyzed are described, for example, in U.S. Pat. No. 5,773,714 to Shead and U.S. Pat. No. 5,166,748 to Dahlquist, which are incorporated herein by reference.

Scanner heads 98, 102 serve as platforms for carrying sensors to detect sheet properties, such as basis weight, in the case of paper. For example, lower scanner head 102 may carry a radiation source, such as a nuclear beta radian source, and upper scanner head 98 may carry a detector. In this case, the sensors can be employed to make basis weight measurements by measuring the radiation intensity incident on the detector when a sheet is present as compared to the beta radiation that is incident upon the detector, when no sheet is present; that is, the basis weight is measured by the beta radiation attenuated by the sheet material.

Alternatively, to measure the moisture content of paper, an infrared radiation source can be positioned in the lower scanner head 102 and the radiation that is transmitted through the paper is captured by a detector that is located in the upper scanner head 98. Analysis of the transmitted radiation yields the moisture content. Exemplary scanning dual head sensors employing radiation source and detectors are described, for example, in U.S. Pat. No. 5,654,799 to Chase et al., U.S. Pat. No. 5,793,486 to Gordon et al., and U.S. Pat. No. 7,494,567 to Haran, which are incorporated herein by reference. While the sensor is illustrated in measuring characteristics of paper, it is understood that the sensor can be employed to detect a variety of components in a number of different materials including, for example, plastics, coated materials, fabrics, and the like.

Interference with the movement of scanner heads 98, 102 by foreign bodies can be detected and acted upon. Where the abnormal occurrence is severe such as in the case of impact by an object, the drive system can be shut down immediately. Less severe situations such as sudden acceleration changes that cause a scanner head to jerk will cause vibrations in the head mountings and drive system that can be detected. The motor drive tuning can be adjusted during regular maintenance.

Positioned preferably in the center of upper scanner head 98 is a vibration sensor 128 such as a three axis Printed Circuit Board (PCB) mounted accelerometer. A preferred accelerometer is model MMA7361L from Freescale Semiconductor, Inc. (Tempe Ariz.). Alternatively, several single-axis accelerometers oriented to provide three-axis sensing can be used. Similarly, lower scanner head 102 includes a three axis PCB mounted accelerometer 138. A feature of the invention is that by positioning the accelerometers in scanner heads 98 and 102, the vibrations propagate through rigid support assemblies 60 and 66, respectively before being sensed by the accelerometers. Each support assembly, which is preferably the only connection between the carriage and scanner head, serves as conduits that effectively channel vibration energy to each of to the sensors. Each three-axis accelerometer converts mechanical vibrations emanating from components of the scanner system located exterior of the sensor head into mechanical signature analog signals. This arrangement which incorporates an accelerometer in each of the dual scanner heads affords independent upper and lower head measurements which will precisely pinpoint and identify the source of potential mechanical problems, for example, in either the upper or lower assemblies faster than purely differential head displacement readings. For instance, with respect to monitoring resonant vibrations, the invention will be superior to relative displacement measurements between the upper and lower sensor heads. This is due to the likely existence of vibration frequencies that affect both the upper and lower support beams and that cause differential frequencies to be measured with the attendant frequency beatings complicating the readings.

The scanner system illustrated in FIG. 5 with the dual scanner heads is particularly suited where the system operates in the transmissive mode in which radiation from a radiation source located in one scanner head is detected by a radiation received located in the other scanner head. With the present invention, neither scanner head needs an alignment or head displacement sensor. In applications where the system operates in the reflective mode, only a single scanner head, with its associated accelerometer is required. In these single-sided scanning systems, the single sensor head houses both the radiation source and radiation receiver so that radiation reflected from the sheet of material is detected by the receiver. Displacement xyz type sensors of the prior art cannot be used with a single sided sensor. With a single sensor head, there is no opposing sensor head surface from which comparative readings can be obtained. In this regard, employing an accelerometer in the present invention is particularly suited for diagnosing motion information to infer issues concerning the support beam.

A technique of implementing the diagnostic process of the prevention invention is to initially operate the scanner system and monitor the vibrational characteristics of the scanner at known conditions ranging from normal or defect-free to abnormal conditions. Vibrational characteristics that are produced by the different components of the scanner systems are sensed by the accelerometers. As the scanner system is operated under normal conditions during transient or steady-state conditions, the accelerometers measured the vibrational characteristics that are then converted into normal reference signatures, that is, signatures of the scanner system components under defect-free operating conditions. Similarly, as the scanner system is operated at known abnormal conditions a corresponding set of abnormal reference signatures is established. The normal and abnormal reference signatures identify the source, location and severity of the conditions. Once a library of reference signatures is created, the scanner system can be readily evaluated continuously by measuring vibrational characteristics produced during actual operations of the system and generating operational signatures that are compared to the reference signatures. A comparison of the signatures will indicate whether the various components in the scanner system are operating normally or abnormally and to what degree. Corrective action can be implemented where the onset of mechanical problems is detected and, in situations where the detected problem is serious the scanning system can be deactivated.

Figure 6:
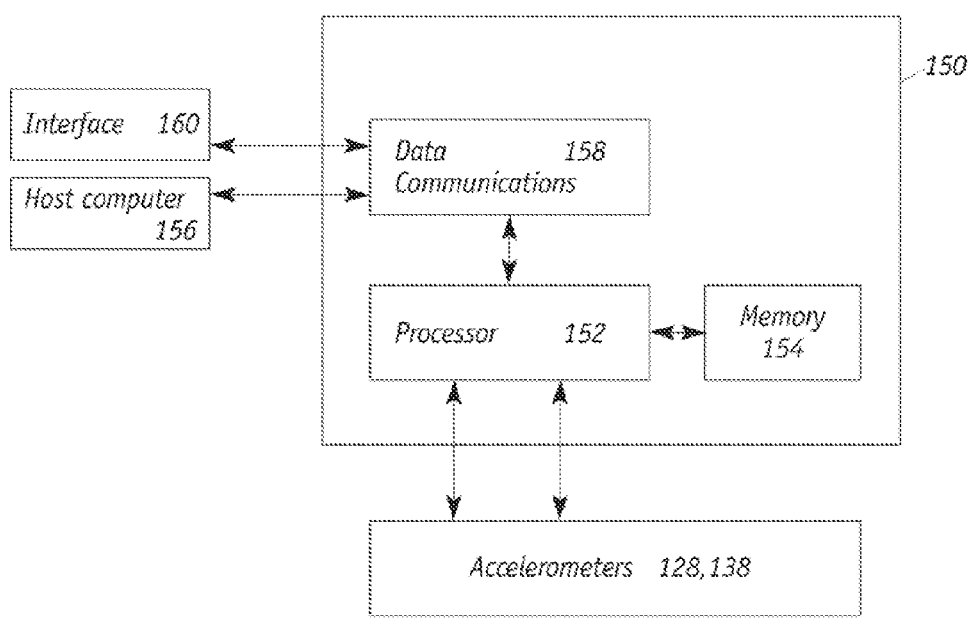
FIG. 6 is a schematic diagram of the operations of the three axis accelerometers.

FIG. 6 depicts operations of the accelerometers 128 and 138 that are located in the scanner head 98 and 102, respectively, (FIG. 5) in diagnosing a scanner system. Diagnostic module 150 includes a processor 152 that is programmed to control and operate the various components in diagnostic module 150. A memory 154 stores vibration analysis data including the library of reference signatures and historical vibration data relating to the scanner system. Data communication system 158 interfaces processor 152 with interface device 160 and host computer 156.

During operations of a scanner system, accelerometers 128, 138 detect vibrations and generate vibration signals that are received by processor 152 which generate vibration signatures corresponding to the vibration signals. Processor 152 accesses memory 154 to identify the source in the scanner system of the vibrations and to determine the condition of the machine component. Command and parameter information are communicated via data communication system 158. Depending on the nature of the problem detected, the command can instruct the host computer 156 to shut down the system or simply display diagnostic information in interface device 160.

The foregoing has described the principles, preferred embodiments and modes of operation of the present invention. However, the invention should not be construed as being limited to the particular embodiments discussed. Thus, the above-described embodiments should be regarded as illustrative rather than restrictive, and it should be appreciated that variations may be made in those embodiments by workers skilled in the art without departing from the scope of the present invention as defined by the following claims.

What is claimed is:

1. A diagnostic system for monitoring a scanning system that detects characteristics of a sheet of material during linear translation along a translation axis of a bi-directionally driven mobile detector device, the diagnostic system comprising:
   (a) the scanning system being monitored which comprises:
      (i) a first elongated member that extends along a first direction wherein the first elongated member supports a first carriage that is mounted thereon;
      (ii) means for driving the first mounted carriage, that supports a first sensor head, along a main scanning direction;
      (iii) a second elongated member that extends along a second direction that is parallel to the first direction wherein the second elongated member supports a second carriage that is mounted thereon; and
      (iv) means for driving the second carriage, that supports a second sensor head, characterized in that the scanning system includes a common drive mechanism comprising a single motor that moves both the first carriage and the second carriage;
   (b) a vibration sensor configured to measure vibrations generated by one or more components of the scanning system and generating vibration signals indicative of operation conditions of the one or more components; and
   (c) means for correlating the vibration signals to modes of operations of the one or more components of the scanning system.

2. The diagnostic system of claim 1 wherein the vibration sensor comprises a three-axis accelerometer that is positioned in the first sensor head.

3. The diagnostic system of claim 2 wherein the accelerometer is configured to measure vibrations generated by the one or more components of the scanning system that are housed exterior of the first sensor head.

4. The diagnostic system of claim 2 wherein the first sensor head is secured to the first carriage by a support assembly through which vibrations generated by the one or more components are channeled to the vibration sensor.

5. The diagnostic system of claim 1 wherein the means for correlating the vibration signals compares the vibration signals to reference signals to determine the state of the one or more components.

6. The diagnostic system of claim 5 wherein the state of the one or more components identifies the location, source and severity of operations for the one or more components.

7. The diagnostic system of claim 1 wherein the vibration sensor comprises (i) a first accelerometer that is positioned in the first sensor head and the first accelerometer is configured to measured vibrations generated by components of the scanning system that are not housed in the first sensor head and a second accelerometer that is positioned in the second sensor head and the second accelerometer is configured to measured vibrations generated by components of the scanning system that are not housed in the second sensor head.

8. The diagnostic system of claim 7 wherein the first accelerator measures vibrations generated by components associated with movement of the first carriage and the second accelerator measures vibrations generated by components associated with movement of the second carriage.

9. The diagnostic system of claim 7 wherein the first accelerometer measures vibrations associated with resonance in the first elongated member and the second accelerometer measures vibrations associated with resonance it the second elongated member.

10. A method of diagnosing a mechanical condition of a scanning system that detects characteristics of a sheet of material during linear translation along a translation axis of a bi-directionally driven mobile detector device, wherein the scanning system being monitored includes (i) a first elongated member that extends along a first direction wherein the first elongated member supports a first carriage that is mounted thereon; (ii) means for driving the first mounted carriage, that supports a first sensor head, along a main scanning direction; (iii) a second elongated member that extends along a second direction that is parallel to the first direction wherein the second elongated member supports a second carriage that is mounted thereon; and (iv) means for driving the second carriage, that supports a second sensor head, characterized in that the scanning system includes a common drive mechanism comprising a single motor that moves both the first carriage and the second carriage; said method comprising the steps of:
   (a) obtaining vibration signatures with a vibration sensor that are characteristic of one or more components of the scanning system; and
   (b) correlating the vibration signatures to modes of operations of the one or more components of the scanning system.

11. The method of claim 10 further comprising step (c) of initiating corrective measures to ameliorated detected malfunctions.

12. The method of claim 10 wherein step (b) comprises determining directional responses of the first carriage and second carriage and determining if the first carriage and second carriage is moving in accordance with commands from a host computer.

13. The method of claim 10 wherein the vibration sensor comprises a three-axis accelerometer that is positioned in the first sensor head.

14. The method of claim 13 wherein the first sensor head is secured to the first carriage by a support assembly through which vibrations generated by the one or more components are channeled to the vibration sensor.

15. The method of claim 10 wherein step (b) identifies the location, source and severity of operations for the one or more components.

16. The method of claim 10 wherein the vibration sensor comprises (i) a first accelerometer that is positioned in the first sensor head and the first accelerometer is configured to measured vibrations generated by components of the scanning system that are not housed in the first sensor head and a second accelerometer that is positioned in the second sensor head and the second accelerometer is configured to measured vibrations generated by components of the scanning system that are not housed in the second sensor head.

17. The method of claim 16 wherein the first accelerator measures vibrations generated by components associated with movement of the first carriage and the second accelerator measures vibrations generated by components associated with movement of the second carriage.

18. The method of claim 16 wherein the first accelerometer measures vibrations associated with resonance in the first elongated member and the second accelerometer measures vibrations associated with resonance in the second elongated member.

19. A diagnostic system for monitoring a scanning system that detects characteristics of a sheet of material during linear translation along a translation axis of a bi-directionally driven mobile detector device, the diagnostic system comprising:
(a) the scanning system being monitored which comprises:
(i) a first elongated member that extends along a first direction wherein the first elongated member supports a first carriage that is mounted thereon; and
(ii) means for driving the first mounted carriage, that supports a first sensor head, along a main scanning direction wherein the means for driving the first mounted carriage includes a motor with a motor shaft that is operatively coupled to a first flexible cable to drive the first mounted carriage;
(b) an encoder configured to track the position of the motor shaft and to generate tracking signals;
(c) a host computer that generates commands to control operations of the scanning system including directional movement of the first mounted carriage and that receives the tracking signals; and
(d) a three-axis accelerometer configured to monitor movement of said means for driving the first mounted carriage and to generate observable acceleration readings that are indicative of a direction of movement of the first carriage, wherein the acceleration readings are independent of the host computer commands.

20. The diagnostic system of claim 19 wherein the scanning system being monitored further comprises:
(iii) a second elongated member that extends along a second direction that is parallel to the first direction wherein the second elongated member supports a second carriage that is mounted thereon; and
(iv) means for driving the second carriage, that supports a second sensor head, wherein the motor shaft that is operatively coupled to a second flexible cable to drive the second mounted carriage and characterized in that the scanning system includes a common drive mechanism comprising a single motor that moves both the first carriage and the second carriage; and
wherein the diagnostic system includes one or more three-axis accelerometers configured to monitor movement of said means for driving the first mounted carriage and said means for driving the second mounted carriage to generate observable acceleration readings that are indicative of directions of movement of the first carriage and second carriage, wherein the acceleration readings are independent of the host computer commands.

21. A method of directional setup of a scanning system that detects characteristics of a sheet of material during linear translation along a translation axis of a bi-directionally driven mobile detector device, wherein the scanning system being monitored includes (i) a first elongated member that extends along a first direction wherein the first elongated member supports a first carriage that is mounted thereon; (ii) means for driving the first mounted carriage, that supports a first sensor head, along a main scanning direction wherein the means for driving the first mounted carriage includes a motor with a motor shaft that is operatively coupled to a first flexible cable to drive the first mounted carriage; (iii) an encoder configured to track the position of the motor shaft and to generate tracking signals; (iv) a host computer that generates commands to control operations of the scanning system including directional movement of the first mounted carriage and that receives the tracking signals; and (v) a three-axis accelerometer configured to monitor movement of said means for driving the first mounted carriage and to generate acceleration readings that are indicative of a direction of movement of the first carriage, said method comprising the steps of:
(a) employing the host computer to generate commands to startup the scanning system such that the first carriage moves back and forth along the main scanning direction in response to directional commands of the host computer;
(b) obtaining vibration signatures with the three-axis accelerometer that are characteristic of a direction of movement of the first carriage and generating observable acceleration readings of the direction of movement wherein the acceleration readings are independent of the host computer commands; and
(c) determining if the first carriage is moving in a direction that is consistent with the host computer directional commands.

22. The method of claim 21 wherein the scanning system being monitored further includes:
(iii) a second elongated member that extends along a second direction that is parallel to the first direction wherein the second elongated member supports a second carriage that is mounted thereon; and
(iv) means for driving the second carriage, that supports a second sensor head, wherein the motor shaft that is operatively coupled to a second flexible cable to drive the second mounted carriage and characterized in that the scanning system includes a common drive mechanism comprising a single motor that moves both the first carriage and the second carriage; and
wherein the diagnostic system includes one or more three-axis accelerometers configured to monitor movement of said means for driving the first mounted carriage and said means for driving the second mounted carriage to generate observable acceleration readings that are indicative of directions of movement of the first carriage and second carriage, wherein the acceleration readings are independent of the host computer commands and wherein
step (a) comprises employing the host computer to generate commands to startup the scanning system such that the first and second carriages move back and forth in synchronized fashion along the main scanning direction in response to directional commands of the host computer;
step (b) comprises obtaining vibration signatures with the one or more three-axis accelerometers that are characteristic of a direction of movement of the first carriage and the second carriage and generating observable acceleration readings of the direction of movement wherein the acceleration readings are independent of the host computer directional commands; and step (c) comprises determining if the first and second carriages are moving in a direction that is consistent with the host computer directional commands.

\* \* \* \* \*